(12) United States Patent
Mitchell et al.

(10) Patent No.: US 10,595,981 B2
(45) Date of Patent: Mar. 24, 2020

(54) COATED SUTURES FOR REDUCING STENT GRAFT ENDOLEAKS

(71) Applicant: Medtronic Vascular, Inc., Santa Rosa, CA (US)

(72) Inventors: Jeffrey Mitchell, Santa Rosa, CA (US);
Keith Perkins, Santa Rosa, CA (US);
Samuel Robaina, Novato, CA (US);
Rajesh Radhakrishnan, Petaluma, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 550 days.

(21) Appl. No.: 15/238,538

(22) Filed: Aug. 16, 2016

(65) Prior Publication Data
US 2018/0049861 A1    Feb. 22, 2018

(51) Int. Cl.
| | | |
|---|---|---|
| *A61F 2/07* | (2013.01) | |
| *A61B 17/06* | (2006.01) | |
| *A61F 2/848* | (2013.01) | |
| *A61L 31/04* | (2006.01) | |
| *A61L 31/14* | (2006.01) | |
| *A61B 17/00* | (2006.01) | |

(52) U.S. Cl.
CPC .......... *A61F 2/07* (2013.01); *A61B 17/06166* (2013.01); *A61F 2/848* (2013.01); *A61L 31/041* (2013.01); *A61L 31/14* (2013.01); *A61L 31/145* (2013.01); *A61L 31/146* (2013.01); *A61B 2017/00898* (2013.01); *A61F 2002/075* (2013.01); *A61F 2002/077* (2013.01); *A61F 2002/8486* (2013.01); *A61F 2210/0057* (2013.01); *A61F 2210/0061* (2013.01)

(58) Field of Classification Search
CPC .... A61L 17/145; A61L 17/00; A61L 2400/04; A61L 33/0064; A61F 2/07; A61F 2002/075; A61B 17/1219
See application file for complete search history.

(56) References Cited

U.S. PATENT DOCUMENTS

| | | | |
|---|---|---|---|
| 6,602,261 B2 * | 8/2003 | Greene, Jr. | ........ A61B 17/1219 606/108 |
| 7,442,205 B2 | 10/2008 | Verhoeven et al. | |
| 2005/0154446 A1 * | 7/2005 | Phillips | ..................... A61F 2/07 623/1.13 |

(Continued)

FOREIGN PATENT DOCUMENTS

| | | |
|---|---|---|
| EP | 2769699 A1 | 8/2014 |
| WO | 2006/023486 A1 | 3/2006 |

OTHER PUBLICATIONS

PCT/US2017/046990, The International Search Report and the Written Opinion of the International Searching Authority, dated Oct. 11, 2017, 12 pages.

(Continued)

*Primary Examiner* — Brian E Pellegrino (57) ABSTRACT

The present technology relates generally to endovascular prostheses. More particularly, the disclosure relates to endovascular prostheses having a graft material and a stent structure attached with a suture, or a seam formed by a suture, where the suture has a coating that expands upon exposure to body fluids. The expansion allows for the coating to fill suture holes in the graft material so as to reduce or eliminate endoleaks.

18 Claims, 6 Drawing Sheets

(56) References Cited

U.S. PATENT DOCUMENTS

2005/0159803 A1    7/2005   Lad et al.
2007/0078480 A1*   4/2007   Belenkaya ......... A61B 17/1219
                                                                    606/200
2009/0149939 A1    6/2009   Godlewski et al.

OTHER PUBLICATIONS

Ahmed, Enas M., "Hydrogel: Preparation, characterization, and applications: A review," *Journal of Advanced Research* (2015) 6, 105-121.

* cited by examiner

COATED SUTURES FOR REDUCING STENT GRAFT ENDOLEAKS

FIELD OF THE INVENTION

The present technology relates generally to endovascular prostheses. More particularly, the disclosure relates to endovascular prostheses having a graft material and a stent structure attached with a suture, or a seam formed by a suture, where the suture has a coating that expands upon exposure to body fluids. The expansion allows for the coating to fill suture holes in the graft material so as to reduce or eliminate endoleaks.

BACKGROUND OF THE INVENTION

Endovascular procedures are successfully used to treat thoracic and abdominal aneurysm. Most endovascular stent grafts consist of metallic stent rings attached to a graft material using sutures. One of the issues associated with this type of stent graft is endoleaks, arising from either a leak through the graft material itself, or a leak through the suture holes in the graft material that result from attaching the graft material to the stent rings.

In order to address these leaks, graft materials have been developed which limit the permeability through the material of the graft. However, there still remains a need to reduce endoleaks that occur through suture holes in the graft material.

BRIEF SUMMARY OF THE INVENTION

In view of the foregoing, provided herein are devices comprising sutures coated with a material which can expand to fill suture holes in a graft material, so as to reduce or eliminate endoleaks.

Embodiments hereof are directed to endovascular prostheses comprising an anchor stent, a tubular body formed from a graft material, wherein the anchor stent is attached to an end of the tubular body, and a body stent attached to the tubular body. Suitably, at least one of the anchor stent and the body stent is attached to the tubular body with a suture having an outer layer that expands in vivo upon exposure to a body fluid.

Also provided herein are endovascular prostheses having a compressed configuration for delivery within a vasculature and a radially-expanded configuration for deployment within a target blood vessel of a patient. Suitably, the prostheses comprise an anchoring structure for engaging an inner wall of the target blood vessel when the prosthesis is in the radially-expanded configuration, a tubular body defining a central lumen from a first end to a second end thereof, wherein the anchoring structure is attached to the first end of the tubular body, and a support ring attached to an outer surface of the tubular body for maintaining the tubular body in the radially-expanded configuration. In embodiments, at least one of the anchoring structure and the support ring is attached to the tubular body with a suture comprised of a material that expands in vivo upon exposure to a body fluid without dissolving.

Further, provided herein are endovascular prostheses comprising a stent structure, and a graft material, wherein the stent structure is attached to the graft material with a suture having a coating that expands upon exposure to an aqueous solution.

BRIEF DESCRIPTION OF DRAWINGS

The foregoing and other features and aspects of the present technology can be better understood from the following description of embodiments and as illustrated in the accompanying drawings. The accompanying drawings, which are incorporated herein and form a part of the specification, further serve to illustrate the principles of the present technology. The components in the drawings are not necessarily to scale.

DETAILED DESCRIPTION OF THE INVENTION

Specific embodiments of the present technology are now described with reference to the figures, wherein like reference numbers indicate identical or functionally similar elements. Unless otherwise indicated, the terms "distal" and "proximal" are used in the following description with respect to the direction of blood flow from the heart and through the vasculature. Accordingly, with respect to a prosthesis or stent, the terms "proximal" and "distal" can refer to the location of portions of the device with respect to the direction of blood flow. For example, proximal can refer to an upstream position or a position of blood inflow, and distal can refer to a downstream position or a position of blood outflow. For example, "distal" or "distally" indicates an apparatus portion distant from, or a direction away from, the heart or along the vasculature in the direction of blood flow. Likewise, "proximal" and "proximally" indicates an apparatus portion near to, or in a direction towards the heart.

The following detailed description is merely exemplary in nature and is not intended to limit the present technology or the application and uses of the present technology. Although the description of embodiments hereof are in the context of treatment of tissue defects in blood vessels, the present technology may also be used in any other body passageways or other blood vessel locations not specifically discussed herein and where it is deemed useful (e.g., other anatomical lumens, such as bronchial and other air passageways, fallopian tubes, bile ducts, etc.). Furthermore, there is no intention to be bound by any expressed or implied theory presented in the preceding technical field, background, brief summary or the following detailed description.

Embodiments of the present technology as described herein can be combined in many ways to treat one or more of many vascular defects such as aneurysms or dissections within a blood vessel, such as the abdominal or thoracic regions of the aorta. The embodiments of the present technology can be therapeutically combined with many known surgeries and procedures, for example, such embodiments can be combined with known methods of accessing the target tissue defects, such as percutaneous access of the abdominal or thoracic regions of the aorta through the femoral artery to deliver and deploy the endoluminal prosthetic devices described herein. Other routes of access to the target regions are also contemplated and are well known to one of ordinary skill in the art.

Endovascular Prostheses Comprising Coated Sutures

In embodiments, described herein are endovascular prostheses. For example, endovascular prosthesis comprising a stent structure and a graft material, wherein the stent structure is attached to the graft material with a suture having a coating that expands upon exposure to an aqueous solution.

Figure 1A:
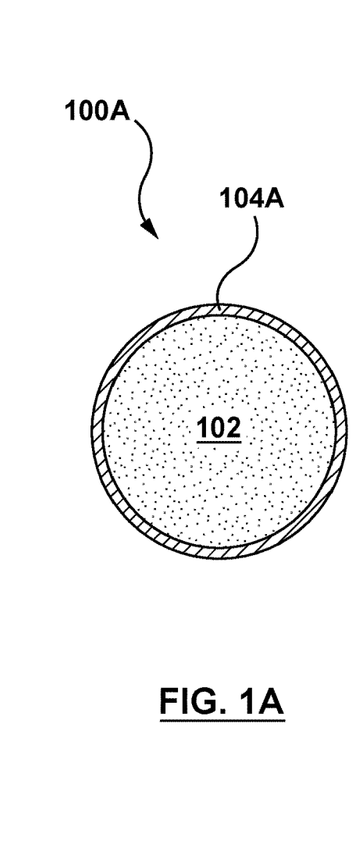
FIGS. 1A-1B are cross-sectional views of a suture having a coating in accordance with an embodiment hereof.
Figures 1B, 1C:
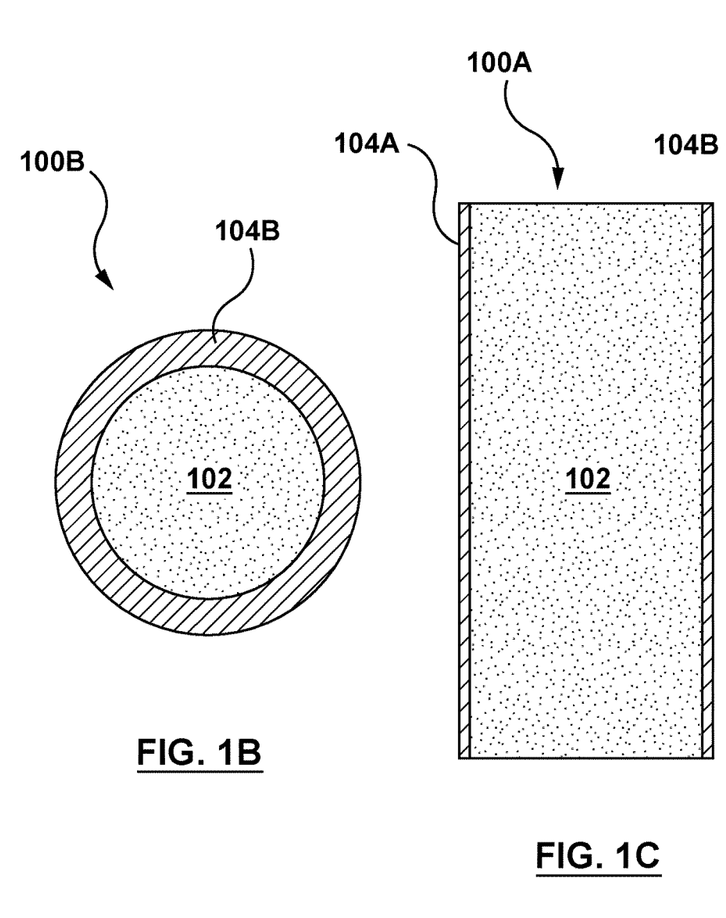
FIGS. 1C-1D are sectional views taken along a length of a suture having a coating in accordance with an embodiment hereof.

FIG. 1A depicts an embodiment of an unexpanded coated suture 100A that includes a suture 102 having a coating 104A. FIG. 1A is a cross-sectional view of suture 102, showing the suture 102 surrounded by coating 104A, which is an outer layer surrounding the suture, and FIG. 1C is a sectional view of the suture 102 and the coating 104A taken along a length of the coated suture 100A. Coated suture 100A may be described as being in an unexpanded state in FIGS. 1A and 1C. The thickness of coating 104A and the relationship in sizes between suture 102 and coating 104A are shown for illustrative purposes only and should not be construed to limit the sizes or relative sizes of the components. Exemplary diameters for suture 102 are known in the art, and generally range from about 0.01 mm to about 1 mm. Exemplary suture diameters for common material sutures is provided below.

| USP designation | Collagen diameter (mm) | Synthetic absorbable diameter (mm) | Non-absorbable diameter (mm) | American wire gauge |
| --- | --- | --- | --- | --- |
| 11-0 | | | 0.01 | |
| 10-0 | 0.02 | 0.02 | 0.02 | |
| 9-0 | 0.03 | 0.03 | 0.03 | |
| 8-0 | 0.05 | 0.04 | 0.04 | |
| 7-0 | 0.07 | 0.05 | 0.05 | |
| 6-0 | 0.1 | 0.07 | 0.07 | 38-40 |
| 5-0 | 0.15 | 0.1 | 0.1 | 35-38 |
| 4-0 | 0.2 | 0.15 | 0.15 | 32-34 |
| 3-0 | 0.3 | 0.2 | 0.2 | 29-32 |
| 2-0 | 0.35 | 0.3 | 0.3 | 28 |
| 0 | 0.4 | 0.35 | 0.35 | 26-27 |
| 1 | 0.5 | 0.4 | 0.4 | 25-26 |
| 2 | 0.6 | 0.5 | 0.5 | 23-24 |
| 3 | 0.7 | 0.6 | 0.6 | 22 |
| 4 | 0.8 | 0.6 | 0.6 | 21-22 |
| 5 | | 0.7 | 0.7 | 20-21 |
| 6 | | | 0.8 | 19-20 |
| 7 | | | | 18 |

In general, the thickness of coating 104A will be on the order of about 1 µm to about 1 mm, or more suitably about 1 µm to about 500 µm, about 10 µm to about 500 µm, about 50 µm to about 500 µm, about 100 µm to about 500 µm, about 100 µm to about 300 µm, or about 10 µm, about 20 µm, about 30 µm, about 40 µm, about 50 µm, about 60 µm, about 70 µm, about 80 µm, about 90 µm, about 100 µm, about 110 µm, about 120 µm, about 130 µm, about 140 µm, about 150 µm, about 160 µm, about 170 µm, about 180 µm, about 190 µm, about 200 µm, about 210 µm, about 220 µm, about 230 µm, about 240 µm, about 250 µm, about 260 µm, about 270 µm, about 280 µm, about 290 µm, or about 300 µm.

In exemplary embodiments, the average dry coating thickness (T) of coating (outer layer) 104A is about 0.1 micrometer to about 25 microns, with a standard deviation ($\sigma$), and a relative standard deviation ($100 \times \sigma/T$) of no greater than about 10 percent.

Figure 1D:
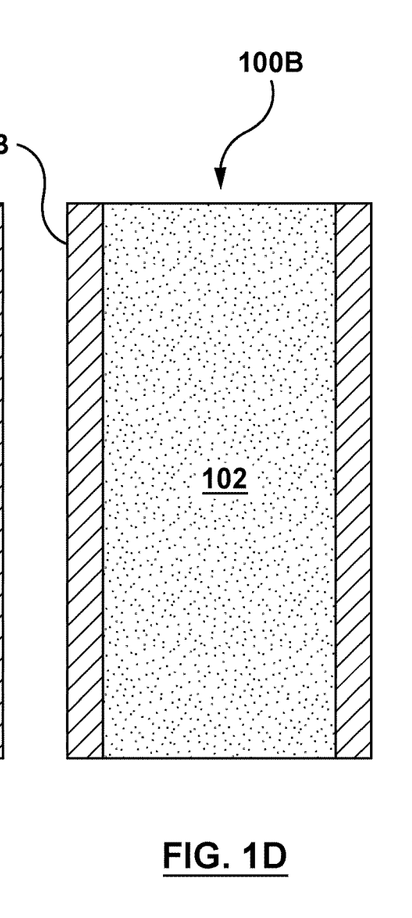

As shown in FIG. 1B, upon exposure to an aqueous solution, coating 104A expands to an expanded coating 104B, and the suture 102 having the expanded coating 104B may be collectively referred to herein as an expanded coated suture 100B. Suitably, coating 104A expands equally in the radial direction along the length of suture 102, as shown in FIG. 1D, which is a sectional view taken along a length of suture 102. Coated suture 100B may be described as being in an expanded state in FIGS. 1B and 1D. Though in other embodiments, coating 104A may expand non-uniformly along the length of suture 102, depending upon characteristics of coating 104A, the environment of the coating 104A/suture 102, and processing of coating 104A. For example, in embodiments, coating 104A may be applied in such a way that expansion occurs only in suture holes and on the outer or exterior portions of the suture, i.e., portions that ultimately will face the wall of a vessel, while not expanding on the interior of the suture, i.e., those portions that face the blood flow passing through the endovascular prosthesis. Such embodiments can be created using differential curing processes, such as ultraviolet light, to prepare coated sutures with an activated polymer (i.e. a polymer that can be expanded) at only desired positions or sections. Etching and masking can also be used to generate coated sutures 100A which have specific coating characteristics.

As used herein, "aqueous solutions" means any solution comprising water, and can be water, saline, a buffer or a body fluid. As used herein "body fluid" refers to a fluid of a mammalian body, including, blood, saliva, urine, plasma, puss, mucus, excretions, etc.

Suitably, coating 104A comprises a polymer, and more suitably a hydrogel polymer, which expands when exposed to an aqueous solution.

A "hydrogel polymer" is a 3-dimensional network of cross-linked, hydrophilic macromolecules capable of being swelled and incorporating about 20 percent to about 95 percent water by weight. Examples of natural hydrogel polymers include fibrin, collagen, elastin, and the like. A hydrogel polymer can be a solution, gel, foam or other material which can be readily associated with suture 102.

Hydrogel polymers, in some instances, are capable of absorbing water (or a body fluid, e.g., blood) relative to its dry weight to greater than 50%, greater than 75%, greater than 100%, greater than 150%, etc. of its dry weight. In other embodiments, the hydrogel polymer may be fully hydrated when containing less than 50% of its dry weight (e.g., less than 45%, less than 40%, etc.). In a dehydrated or low volume state, a hydrogel polymer can, in some instances, be fairly rigid; however with certain compositions, the hydrogel polymer can exhibit increased flexibility as water content increases.

Exemplary hydrogel polymers include polyethylene oxide, polyvinyl alcohol, polyacrylic acid, polypropylene fumarate-co-ethylene glycol, and polypeptides. Agarose, alginate, chitosan, collagen, fibrin, gelatin, and hyaluronic acid are naturally-derived polymers that can also be used for this purpose. For example, hydrogel polymers suitably comprise poly(hydroxyethyl methacrylate), poly-2-hydroxyethylmethacrylate (p-HEMA) and copolymers thereof, poly(vinylpyrrolidinone) (PVP), poly-N-vinyl-pyrrolidone (pNVP) hydrogels, pHEMA/pNVP copolymer, polyvinyl alcohol (PVA) hydrogels, poly(acrylamide) (pAM), poly (acrylic acid) (pAA), and other similar materials.

Methods of applying coating 104A to suture 102 include spraying (spray coating), spin-coating (electrospinning), layering, printing, painting, rolling, or otherwise coating onto suture 102. Suture 102 can also be dipped into a solution, slurry or suspension of coating 104A (e.g., a hydrogel polymer) so as to coat suture 102 (dip coating). In other embodiments, it is possible to co-form coating 104A and suture 102 together so as to prepare an integrated coating-suture material structure, such as by an extrusion process. In additional embodiments, suture 102 can itself be formed of a material useful as coating 104A, for example, a hydrogel.

In embodiments, the coating 104A is applied to suture 102 in a liquid, gel, foam, suspension other flowable form, and then subsequently dried, cured, or otherwise associated with suture 102 so as to provide a final product which can be stored and manipulated.

Suitably, coating 104A expands to expanded coating 104B in vivo upon exposure to a body fluid. That is, when suture 102 with coating 104A is introduced into a body (e.g., mammal such as a human), it is exposed to a body fluid such as blood, and expands to expanded coating 104B.

Figure 2A:
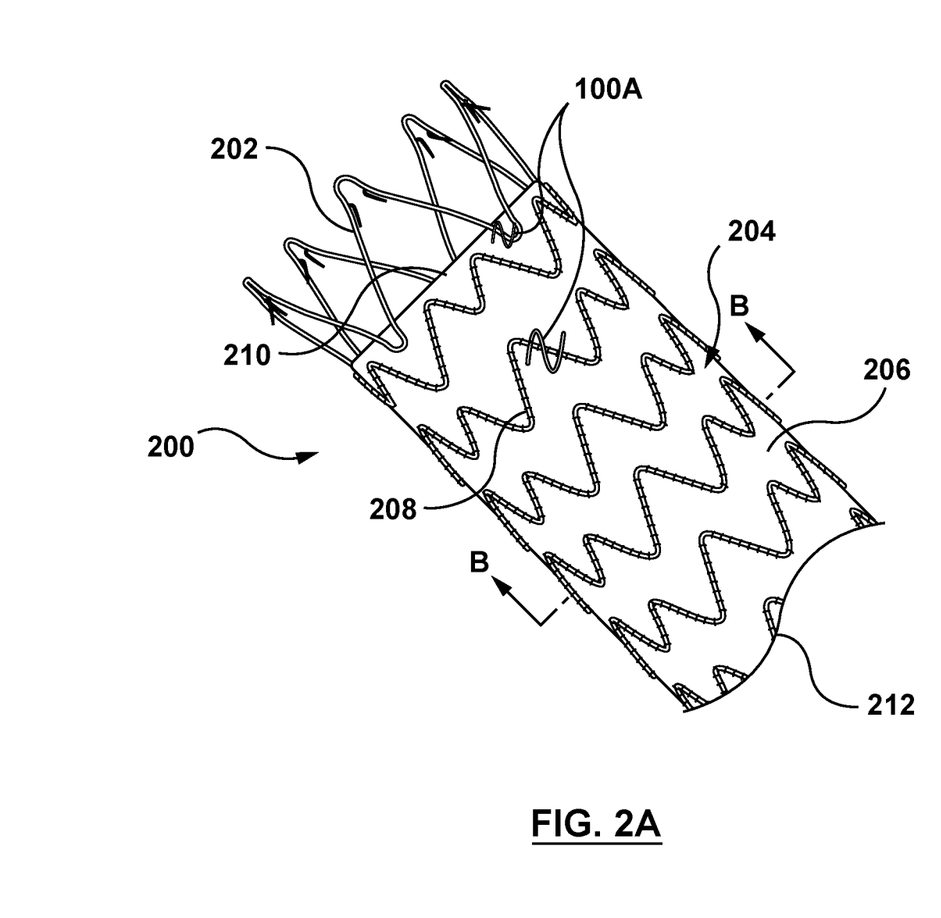
FIG. 2A is an endovascular prosthesis in accordance with an embodiment hereof.

FIG. 2A depicts an endovascular prosthesis 200 in embodiments described herein and generally includes a stent structure (e.g. body stent 208 and/or anchor stent 202) and graft material 206. As shown in FIG. 2A, the stent structure (e.g., body stent 208) is suitably attached to graft material 206 with 102 suture having coating 104A that expands to expanded coating 104B upon exposure to an aqueous solution (suture 102 having coating 104A is also referred to as coated suture 100A herein).

Body stents 208 can be provided as rings (i.e., ring stents) or other expandable features that can be self-expanding and/or balloon expandable as is known in the art. The term "self-expanding" is used to convey that the structures are shaped or formed from a material that can be provided with a mechanical memory or shape memory to return the structure from a radially-compressed or constricted delivery configuration to a radially-expanded configuration for deployment. Non-exhaustive exemplary self-expanding materials include stainless steel, a super-elastic metal such as a nickel titanium alloy or nitinol, various polymers, or a so-called super alloy, which may have a base metal of nickel, cobalt, chromium, or other metal. Mechanical memory may be imparted to a wire or other stent structure, such as anchor stent 202, by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

Figure 3:
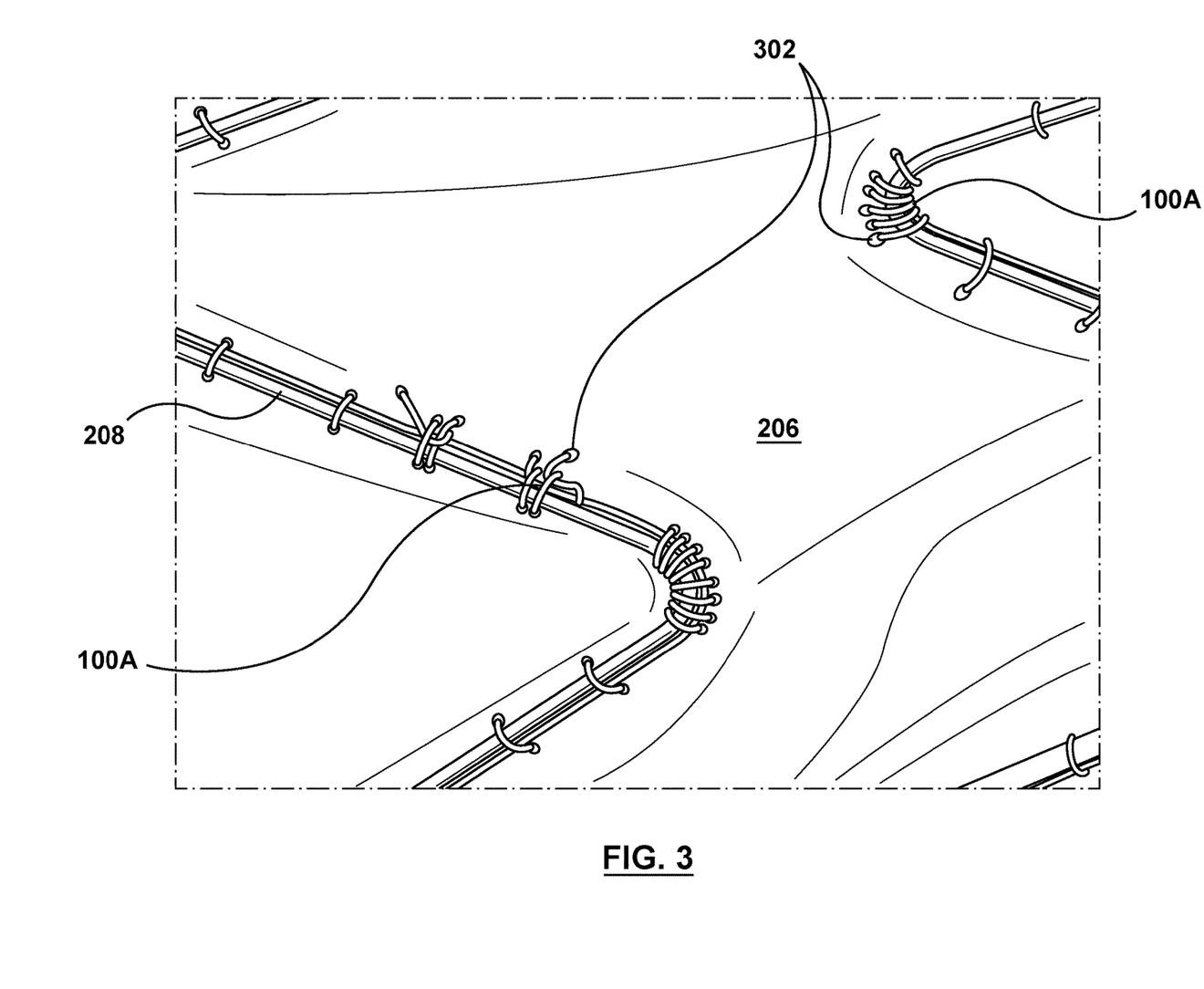
FIG. 3 is a close-up view of an endovascular prosthesis in accordance with an embodiment hereof.

FIG. 3 is an enlarged view of a portion of the endovascular prosthesis 200 that shows various suture holes 302 formed during attachment of the stent structure (e.g., body stent 208) to graft material 206 with coated suture(s) 100A. Coated sutures 100A are shown in an unexpanded state, thus suture holes 302 are shown as not substantially filled, or in other words as having a gap, a space or a void between the coated suture 100A and the perimeter of the suture hole 302. As used herein, "substantially filled" when referring to expanded coating 104B filling suture holes 302 means that the expanded coated suture 100B fills at least about 50%, and more suitably about 75% to about 100%, of the volume of a suture hole 302. That is, about 75% to about 100% (i.e., all) of the volume of openings of suture holes 302 are filled by the expanded coated suture 100B, including about 50%, about 60%, about 70%, about 75%, about 80%, about 85%, about 90%, about 95%, about 96%, about 97%, about 98%, about 99%, or about 100% of openings of suture holes 302 are filled.

Figure 4A:
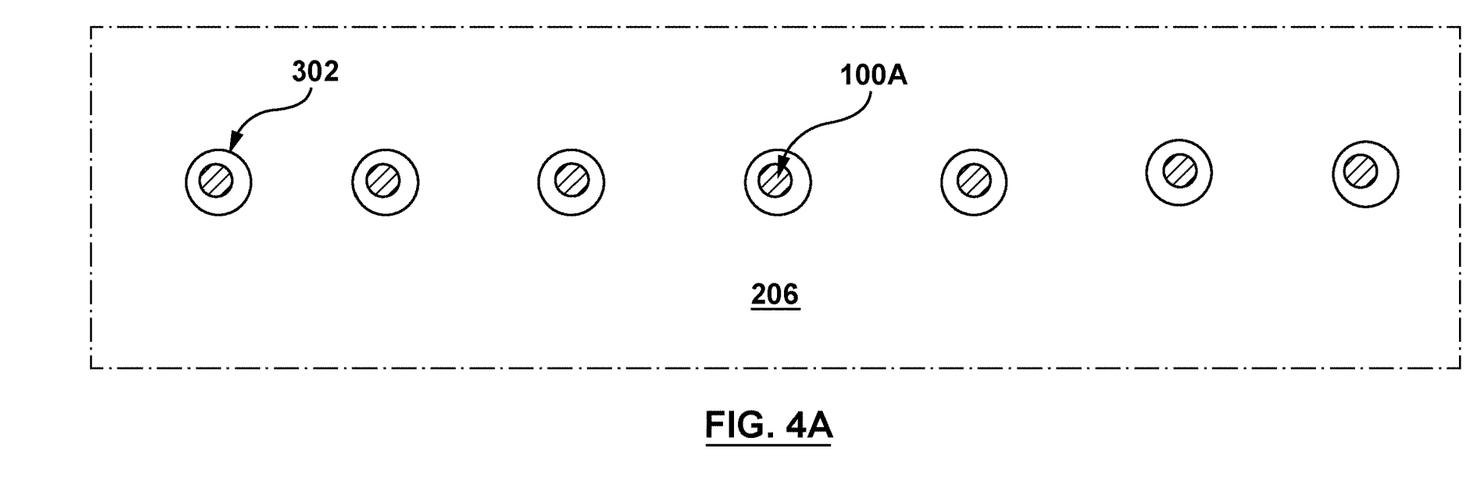
FIGS. 4A-4B are close-up views of an endovascular prosthesis in accordance with an embodiment hereof.
Figure 4B:
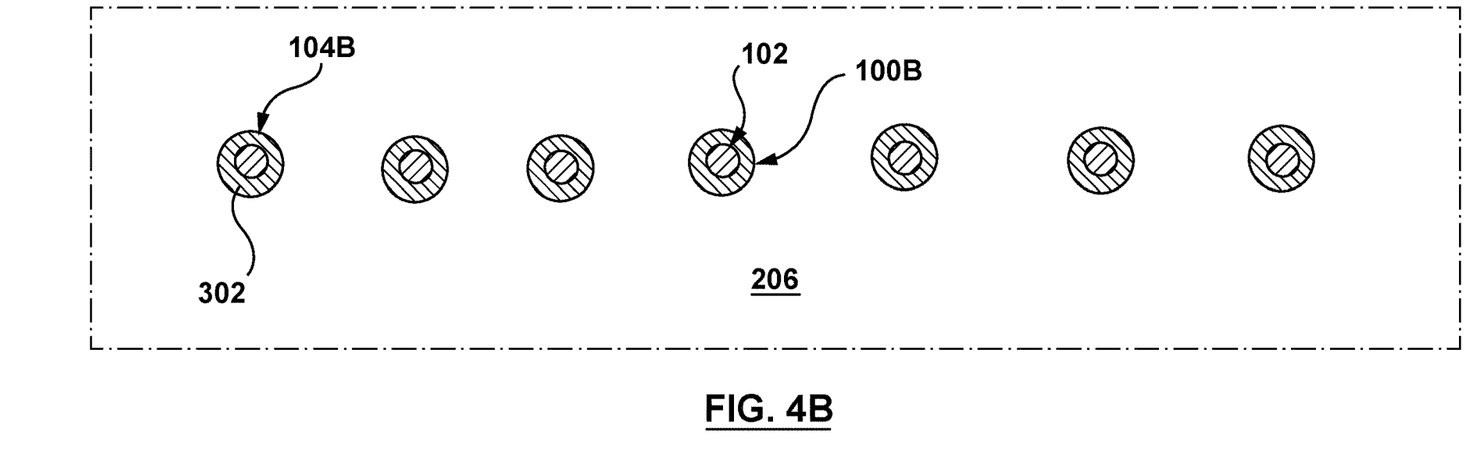

FIG. 4A is a schematic representation of a unexpanded coated suture 100A within suture holes 302 of a graft material 206, and FIG. 4B is a schematic representation of the expanded coated suture 100B in its expanded state within suture holes 302 of the graft material 206. As shown in FIG. 4B, expanded coating 104B substantially fills suture holes 302 formed in graft material 206.

Figure 5:
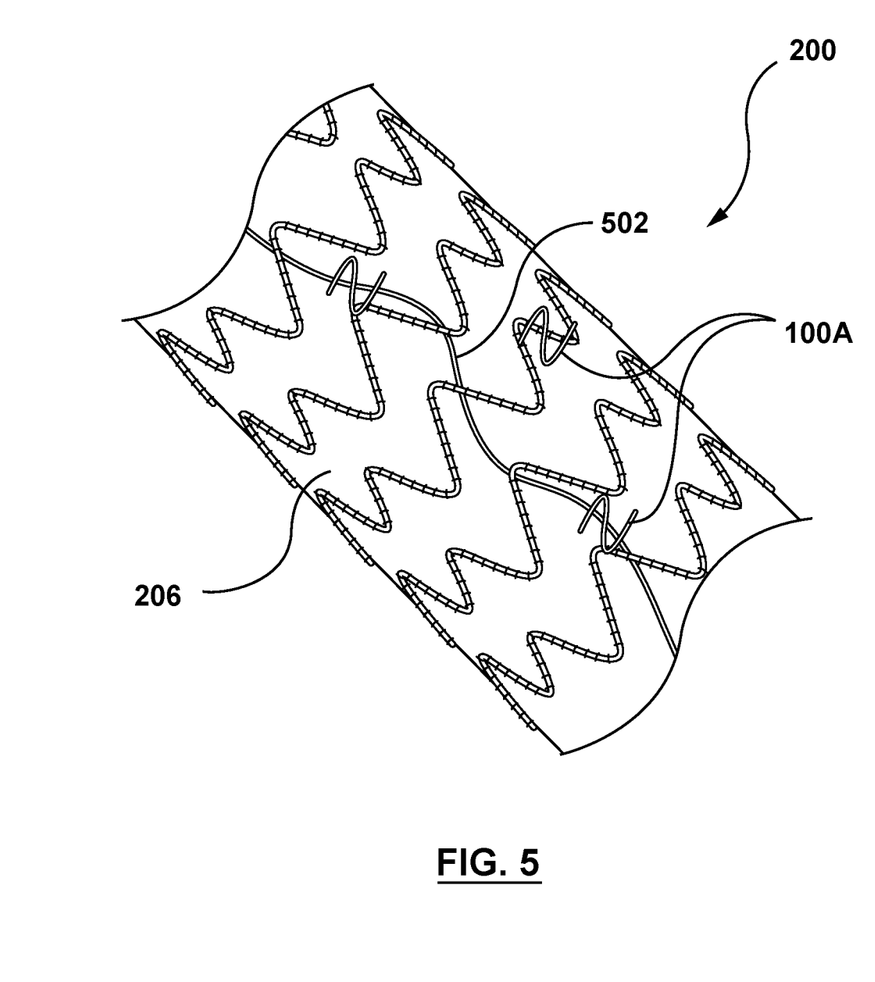
FIG. 5 is a close-up view of an endovascular prosthesis in accordance with an embodiment hereof.

As described herein and as illustrated in FIG. 5, prosthesis 200 can also include a seam 502, which is a line of stitches joining edges of graft material 206 (suitably forming a tubular body as described herein), where seam 502 is formed by suture 102 having coating 104A that expands upon exposure to an aqueous solution. In embodiments, as shown in FIG. 5, prosthesis 200 can comprise at least a first coated suture 100A attaching the stent structure to graft material 206, as well as at least a second coated suture 100A forming seam 502. It should be noted that multiple coated sutures 100A will generally be used to generate seam 502 and to attached stent structure to graft material 206, and only limited coated sutures 100A are shown for illustrative purposes.

In further embodiments, for example as shown in FIG. 2A, endovascular prosthesis 100 may be described as having an anchor stent 202 and a tubular body 204 formed from graft material 206. Suitably, anchor stent 202 is attached to an end, e.g., proximal end 210, of the tubular body 204. Anchor stent 202 is an anchoring structure for engaging an inner wall of a target blood vessel when the prosthesis 200 is in a radially-expanded or deployed configuration.

As shown in FIG. 2A, endovascular prosthesis 200 suitably may also include one or more body stent 208 attached to the tubular body 204. In embodiments, at least one of anchor stent 202 and the one or more body stent 208 is attached to tubular body 204 with one or more suture 102 having an outer layer or coating 104A that expands in vivo upon exposure to a body fluid. Suitably, anchor stent 202 is attached to the tubular body 204 with the coated suture 100A at proximal end 210 of the endovascular prosthesis 200. The one or more body stent 208 is/are suitably a support ring attached to an outer surface of the tubular body 204 for maintaining the tubular body in a radially-expanded or deployed configuration.

Figure 2B:
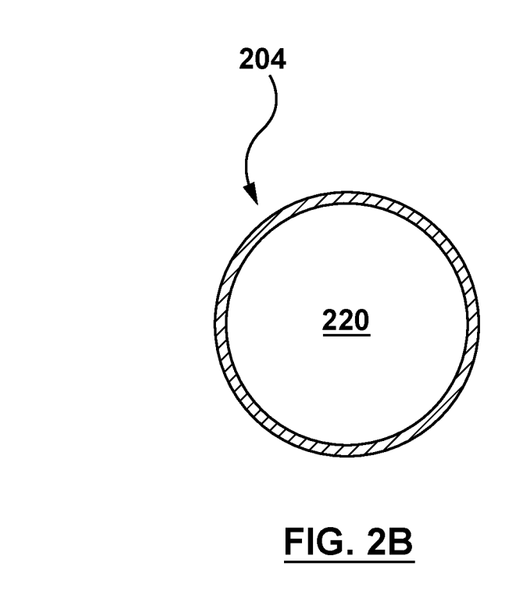
FIG. 2B is a cross-sectional view of the endovascular prosthesis of FIG. 2A taken along line B-B therein in accordance with an embodiment hereof.

Tubular body 204 is suitably cylindrical in shape. In embodiments, tubular body 204 has a uniform cross-sectional diameter (see FIG. 2B), though in other embodiments, tubular body 204 can have a diameter that increases or decreases over the length of the structure, either uniformly or non-uniformly. In embodiments, for example, tubular body 204 can have a larger diameter at one end and a smaller diameter at an opposite end. In embodiments, tubular body 204 may be a single tube formed of a graft material having a generally longitudinally extending seam 502. In other embodiments, a tubular body may be formed of two or more tubular sections, and can be composed as a single structure or multiple structures, suitably joined by one or more seams 502, as described herein.

Examples of body fluids are described herein, as are the expansion of outer layer or coating 104A to expanded outer layer or expanded coating 104B.

As described throughout, the outer layer or coating 104A of suture 102 when expanded to expanded outer layer or coating 104B, substantially fills suture holes 302 formed by suture 102 in graft material 206 of tubular body 204 during attachment of the at least one of anchor stent 202 and body stent 208.

As described herein, outer layer or coating 104A suitably comprises a hydrogel polymer. In further embodiments, outer layer or coating 104A can comprise a hydrophilic foam. As described throughout, outer layer or coating 104A expands when exposed to an aqueous solution, for example blood.

Examples of hydrogel polymers which can be used in outer layer 104A are described herein, and suitably include polymers such as, but not limited to, poly(hydroxyethyl methacrylate) (pHEMA), poly(vinylpyrrolidinone) (PVP), poly(acrylamide) (pAM), and poly(acrylic acid) (pAA), as well as derivatives, mixtures and copolymers thereof.

Examples of hydrophilic foams which can be used in outer layer 104A include, but are not limited to, poly (urethane), poly(ethylene), poly(vinyl alcohol), poly(acrylonitrile) hydrogel, styrene/poly(vinyl-pyrolodone) (PVP) copolymer, and poly(acrylic) acid copolymer, as well as derivatives, mixtures and copolymers thereof.

Suitable materials for use in forming suture 102 include those known in the art, such as, poly(ester) and poly(tetrafluoroethylene).

As described herein and as shown in FIG. 5, endovascular prosthesis 200 can also further comprise seam 502 joining longitudinally extending edges of graft material 206 to form tubular body 204. Suitably, seam 502 is formed by at least a second suture 102 having an outer layer or coating 104A that expands in vivo to an expanded outer layer or expanded coating 104B, upon exposure to a body fluid.

The outer layer of the second suture when expanded substantially fills suture holes 302 formed in graft material 206 by suture 102 along seam 502 thereof. This expansion and substantial filling of suture holes 302 is described herein and shown in an illustrative manner in FIGS. 4A-4B.

Exemplary materials for use as graft material 206 include a flexible sheet of a material such as, but not limited to, poly(tetrafluoroethylene) (PTFE), expanded PTFE (ePTFE), ultra-high-molecular-weight poly(ethylene) (UHMWPE), poly(urethane) and poly(ester), and derivatives, mixtures and co-polymers thereof.

Figure 6A:
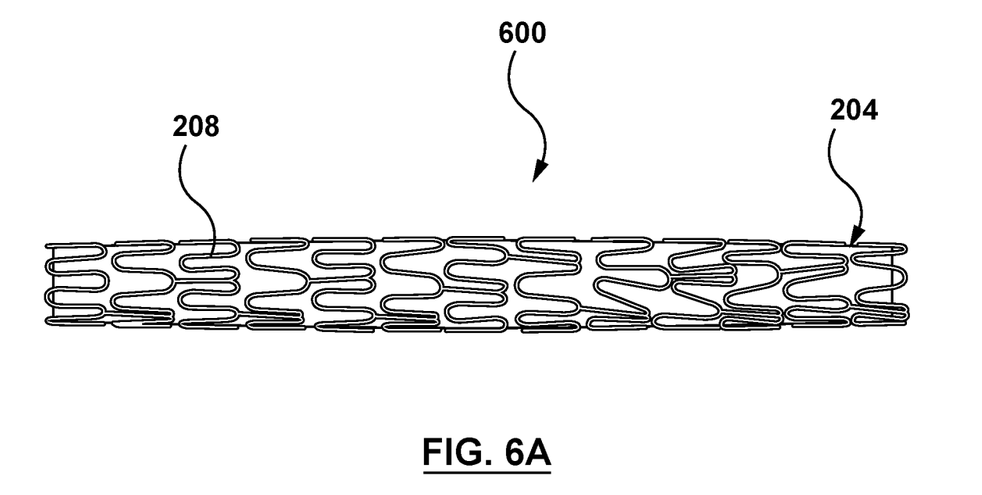
FIG. 6A depicts a prosthesis in accordance with an embodiment hereof in a compressed delivery configuration.
Figure 6B:
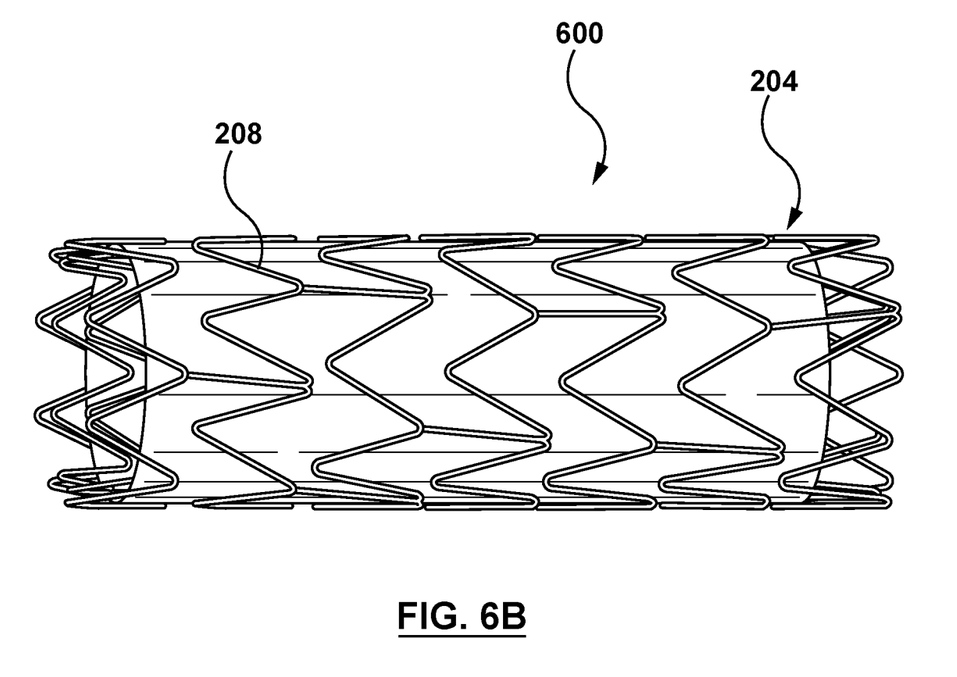
FIG. 6B depicts the prosthesis of FIG. 6A in a radially expanded or deployed configuration.

Also provided herein are endovascular prostheses having a compressed or delivery configuration for delivery within a vasculature and a radially-expanded or deployed configuration for deployment within a target blood vessel of a patient. FIG. 6A shows a prosthesis 600 having a compressed configuration and FIG. 6B shows prosthesis 600 in a radially expanded configuration. Suitably, prosthesis 600 comprises an anchoring structure (e.g., anchor stent 202) for engaging an inner wall of the target blood vessel when the prosthesis is in the radially-expanded configuration. Prosthesis 600 suitably also comprises tubular body 204 defining central lumen 220 (see FIG. 2B) from a first end (e.g., proximal end 210) to a second end (e.g., distal end 212), wherein the anchoring structure is attached to the first end of the tubular body.

Endovascular prosthesis 600 also further comprises a support ring (e.g., a stent structure such as body stent 208), attached to an outer surface of tubular body 204 for maintaining the tubular body in the radially-expanded configuration.

Suitably, at least one of the anchoring structure and the support ring is attached to tubular body 204 with a coated suture 100A that includes a material that expands in vivo upon exposure to a body fluid (i.e., outer layer or coating 104A). In exemplary embodiments, outer layer or coating 104A does not dissolve when contacted with a body fluid that is it maintains its structural integrity when exposed to enzymes, bacteria and other components present in blood.

At least a portion of the coated suture 100A, i.e., coating 104A, when expanded to expanded coating 104B, substantially fills suture holes 302 formed in graft material 206 (see FIGS. 4A-4B) of tubular body 204 during attachment of the at least one of the anchoring structure and the support ring. In further embodiments where one or more seam(s) 502 is/are present, joining edges of graft material 206 to form tubular body 204, seam 502 is formed by a second suture 102 comprised of a material (e.g., coating 104A) that expands in vivo upon exposure to a body fluid without dissolving.

Exemplary materials for graft material, suture and materials that expand in vivo, including hydrogel polymers, are described throughout.

Suitably, prior to implantation of endovascular prosthesis in accordance herewith, such as during storage, handling and delivery to a treatment site, coating 104A is in a non-expanded state and capable of expanding to expanded coating 104B following introduction into or implantation within a target blood vessel of a patient. When the endovascular prosthesis is introduced in a target blood vessel, water/blood is able to be absorbed within coating 104A (e.g., a hydrogel polymer) and hydrate the polymer, causing the coating to expand to expanded coating 104B. In a "non-expanded state" coating 104A suitably contains less than 10% by weight water. When contacted with water (e.g., blood), the coating 104A swells or expands to an "expanded state," thereby occupying a larger volume than in its non-expanded state. In this "expanded state" as expanded coating 104B is able to fill an empty volume, suture hole 302 formed around suture 102 when a stent structure is secured to graft material 206, or along a seam(s) 502.

In further embodiments, coating 104A can be exposed to an aqueous solution prior to implantation within a target blood vessel of a patient, allowing for the expansion to expanded coating 104B, thereby substantially filling any suture holes 302 in graft material even before the endovascular prosthesis is implanted. In such embodiments, suitably this pre-expansion of coating 104A occurs very close in time before implantation in the body of a patient, for example minutes (e.g., 5 to 30 minutes or less), before implantation.

In further embodiments, coating 104A, in addition to a hydrogel polymer, can also further comprise a stabilizing polymer. As used herein "stabilizing polymer" refers to a polymer which provides an additional structure to coating 104A, such that expansion of the coating, e.g., a hydrogel polymer, is limited or constrained so as to help prevent embolization of the hydrogel polymer. The stabilizing polymer can be a co-mixture with the hydrogel polymer, or can be coated under or suitably on top of the hydrogel polymer (i.e., with hydrogel polymer directly contacting the suture). Exemplary stabilizing polymers include various biocompatible polymers, including for example, poly(ethylene terephthalate) and poly(urethane).

In still further embodiments, coating 104A can further comprise with a biologically active agent. As used herein "biologically active agent" refers to a composition or substance that has an effect on living tissue. Biologically active agents include, for example, therapeutic agents, which are substances that tend to prevent and/or overcome disease and/or promote recovery. As such, biologically active agents also include, for example, biologically active molecules (biomolecules) such as drugs. In exemplary embodiments, the biologically active agents which can be utilized in the embodiments described herein include, but are not limited to, collagen, fibrin, thrombin, dipyridamole, heparin, anti-platelet drugs, anti-thrombogenic drugs, anti-proliferative drugs, and anti-mitotic drugs. Suitably, the biologically active agent is a pro-thrombotic material such as collagen fibrin or thrombin. Exemplary bioactive agents are disclosed in U.S. Pat. No. 7,442,205, the disclosure of which is incorporated by reference herein in its entirety, and which is adapted to the various embodiments herein.

Biologically active agents can be utilized with the endovascular prosthesis by adding the biologically active agent to a hydrogel polymer solution prior to applying, or by applying the biologically active agent to a hydrogel polymer layer already associated with the suture. The biologically active agent may be applied in either a dry or the wet state. Application of the biologically active agent in the wet or swollen state suitably provides for more uniform distribution throughout the hydrogel composition. Suitable application methods include, for example, dip coating. Biologically active agents may be added to endovascular prostheses as described herein to provide, for example, biocompatible surfaces. When biologically active agents are used, they are typically added in about 0.1 percent by weight to about 25 percent by weight based on the weight of the hydrogel polymer that is utilized.

In further embodiments, coating 104A may be selected and formulated to controllably release biologically active agents at a desired rate. The rate of release may depend on, for example, the amount and type of biologically active agent present in the coating 104A and the temperature and conditions of the desired release. The rate of release may also depend on the properties of the selected hydrogel polymer including, for example, solubility and polarity. Other factors may also affect the rate of release including, for example, crosslink density.

In still further embodiments, coating 104A can further comprise a bioabsorbable polymer. As used herein, a "bioabsorbable polymer" is a polymer which is readily degraded to components which can be easily adsorbed or otherwise cleared from the body. Examples of bioabsorbable polymers include, but are not limited to, poly(lactic-co-glycolic acid), poly(lactic acid) and poly(glycerol sebacate).

In embodiments hereof, the endovascular prostheses can comprise the recited components, consist of the recited components (i.e., no other components may be included) or consists essentially of the recited components. In embodiments that consist essentially of the recited components, the endovascular prostheses described herein contain the specified materials and those that do not materially affect the basic and novel characteristics of the endovascular prostheses. Such materials that do not materially affect the basic and novel characteristics would include materials that do not impact the ability of coating 104A associated with suture 102 of the endovascular prostheses to take up an aqueous solution, and expand to an expanded state, thus allowing expanded coating 104B to substantially fill suture holes 302 in graft material 206. Examples of such materials that do not materially affect the basic and novel characteristics may include other polymers, stabilizing agents, bioactive agents, etc.

In additional embodiments, the coatings described herein can used to coat sutures which attach the suprarenal/exposed stent, seal stent, and (radio-opaque) RO markers to graft materials. Coating of such sutures with the expandable coatings described herein allow for the filling gaps in the materials, thereby reducing type I endoleaks in the seal region, or leaks around the different components for a parallel graft implant.

In further embodiments, the coatings described herein can be utilized with sutures for the attachment of heart valves to graft material, or uses in other surgical or implantable applications where the expansion of coatings surrounding sutures will aid in filling gaps or defects.

Reduction of Endoleaks Using Coated Sutures

Endoleaks are characterized by persistent blood flow within an aneurysm sac following endovascular aneurysm repair. In successful endovascular aneurysm repair, an aortic stent-graft used suitably excludes the aneurysm from the circulation by providing a conduit for blood to bypass the sac, and continue to flow through the vessel, and to any branch vessels.

There are several causes of endoleak and they are generally be classified into five types as follows (see, e.g., radiopaedia.org/articles/endoleak):

Type I: leak at graft attachment site, which can be proximal, distal, or iliac occlude;

Type II: aneurysm sac filling via branch vessel, which can impact a single vessel, or two vessels or more;

Type III: leak through a defect in a graft, which can include junctional separation of the modular components of a graft, as well as fractures or holes involving the graft;

Type IV: leak through graft fabric as a result of graft porosity; and

Type V: continued expansion of aneurysm sac without demonstrable leak on imaging (a.k.a. endotension).

Type I endoleaks occur as a result of an inadequate seal at the site of the graft attachment. It may occur at the proximal end, distal end or where the components overlap. Blood flow leaks alongside the graft into the aneurysm sac. They are often the result of unsuitable patient (aneurysm) selection or device selection, but can also occur if the graft migrates.

Type II endoleaks are the most common after an abdominal aortic repair. Retrograde flow through branch vessels continue to fill the aneurysm sac. The most common culprit vessels are lumbar arteries, inferior mesenteric artery or internal iliac artery. Embolization of the branch vessel is indicated if the aneurysm sac continues to expand in size.

Type III endoleaks are caused by mechanical failure of the stent-graft. There may be a fracture of the stent-graft, hole or defect on the graft fabric, or junctional separation of the modular components. Causes may relate to defective device material, extreme angulation of a segment predisposing to fracture, or improper overlap of the modular components during insertion.

Type IV endoleaks occur when blood leaks across the graft due to its porosity.

Type V "leak" (also referred to as endotension) is not a true leak but is defined as continued expansion of the aneurysm sac without evidence of a leak site. It is also referred to as endotension. It is believed to be due to pulsation of the graft wall with transmission of the pulse wave through the perigraft space (aneurysm sac) to the native aneurysm wall.

In embodiments described herein, suitably the endovascular prostheses described herein are useful in reducing Type IV endoleaks, or in embodiments, Type III endoleaks. Suture holes 302 in graft material 206 made during suturing of or sewing on a stent structure (e.g., anchoring stent 202 or body stent 208), are substantially filed by the expansion of the outer layer or coating 104A to expanded coating 104B, when exposed to an aqueous solution, such as when implanted in vivo and exposed to a body fluid such as blood.

The endovascular prostheses described herein are suitably used for treatment of mammalian patients, including for example, humans, dogs, cats, pigs, sheet, cows, etc. Suitably the patients are human patients.

While various embodiments have been described above, it should be understood that they have been presented only as illustrations and examples of the present technology, and not by way of limitation. It will be apparent to persons skilled in the relevant art that various changes in form and detail can be made therein without departing from the spirit and scope of the present technology. Thus, the breadth and scope of the present technology should not be limited by any of the above-described embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. An endovascular prosthesis comprising:
    an anchor stent;
    a tubular body defining a central lumen from a first end to a second end thereof, having a surface for facing an inner wall of a target blood vessel, and formed from a graft material, wherein the anchor stent is attached to an end of the tubular body; and
    a body stent attached to the tubular body,
    wherein at least one of the anchor stent and the body stent is attached to the tubular body with a suture having an outer layer activated or generated to only expand at desired positions or sections in vivo upon exposure to a body fluid,
    wherein the outer layer of the suture expands only
        on portions of the suture disposed within suture holes that formed in the graft material of the tubular body during attachment of the at least one of the anchor stent and the body stent, and
        on portions of the suture facing the inner wall of the target blood vessel.

2. The prosthesis of claim 1, wherein the outer layer of the suture when expanded substantially fills the suture holes that formed in the graft material of the tubular body during attachment of the at least one of the anchor stent and the body stent.

3. The prosthesis of claim 2, wherein the outer layer comprises one of a hydrogel polymer and a hydrophilic foam.

4. The prosthesis of claim 3, wherein the hydrogel polymer is selected from the group consisting essentially of poly(hydroxyethyl methacrylate) (pHEMA), poly (vinylpyrrolidinone) (PVP), poly(acrylamide) (pAM), and poly (acrylic acid) (pAA).

5. The prosthesis of claim 3, wherein the hydrophilic foam is selected from the group consisting essentially of poly (urethane), poly(ethylene), poly(vinyl alcohol), poly(acrylonitrile) hydrogel, styrene/poly(vinyl-pyrolodone) (PVP) copolymer, and poly(acrylic) acid copolymer.

6. The prosthesis of claim 3, wherein the suture is formed from one of poly(ester) and poly(tetrafluoroethylene).

7. The prosthesis of claim 1, wherein a seam joins edges of the graft material to form the tubular body and the seam is formed by a second suture having an outer layer that expands in vivo upon exposure to a body fluid, and
    wherein the outer layer of the second suture expands only
        on portions of the second suture disposed within suture holes that formed in the graft material along the seam thereof, and
        on portions of the second suture facing the inner wall of the target blood vessel.

8. The prosthesis of claim 7, wherein the outer layer of the second suture when expanded substantially fills the suture holes that formed in the graft material along the seam thereof.

9. The prosthesis of claim 1, wherein the graft material is a flexible sheet of a material selected from the group consisting essentially of poly(tetrafluoroethylene) (PTFE), expanded PTFE (ePTFE), ultra-high-molecular-weight poly (ethylene) (UHMWPE), poly(urethane) and poly(ester).

10. An endovascular prosthesis having a compressed configuration for delivery within a vasculature and a radially-expanded configuration for deployment within a target blood vessel of a patient, the prosthesis comprising:
    an anchoring structure for engaging an inner wall of the target blood vessel when the prosthesis is in the radially-expanded configuration;
    a tubular body defining a central lumen from a first end to a second end thereof, wherein the anchoring structure is attached to the first end of the tubular body; and
    a support ring attached to an outer surface of the tubular body for maintaining the tubular body in the radially-expanded configuration,
    wherein at least one of the anchoring structure and the support ring is attached to the tubular body with a suture comprised of a material activated or generated to only expand at desired positions or sections in vivo upon exposure to a body fluid without dissolving, and
    wherein the material of the suture expands only
        on portions of the suture disposed within suture holes that formed in a graft material of the tubular body during attachment of the at least one of the anchoring structure and the support ring, and
        on portions of the suture facing the inner wall of the target blood vessel.

11. The prosthesis of claim 10, wherein at least the portions of the suture disposed within suture holes, when expanded, substantially fill the suture holes that formed in the graft material of the tubular body during attachment of the at least one of the anchoring structure and the support ring.

12. The prosthesis of claim 11, wherein a seam joins edges of the graft material to form the tubular body and the seam is formed by a second suture comprised of a material that expands in vivo upon exposure to a body fluid without dissolving, and
    wherein the material of the second suture expands only
        on portions of the second suture disposed within suture holes that formed in the graft material along the seam thereof, and
        on portions of the second suture facing the inner wall of the target blood vessel.

13. The prosthesis of claim 12, wherein the graft material is a flexible sheet of a material selected from the group consisting essentially of poly(tetrafluoroethylene) (PTFE), expanded PTFE (ePTFE), ultra-high-molecular-weight poly (ethylene) (UHMWPE), poly(urethane) and poly(ester).

14. The prosthesis of claim 10, wherein the material comprises one of a hydrogel polymer and a hydrophilic foam.

15. The prosthesis of claim 14, wherein a remainder of the suture is formed from a material selected from the group of poly(ester) and poly(tetrafluoroethylene).

16. The prosthesis of claim 14, wherein the hydrogel polymer is selected from the group consisting essentially of poly(hydroxyethyl methacrylate) (pHEMA), poly (vinylpyrrolidinone) (PVP), poly(acrylamide) (pAM), and poly (acrylic acid) (pAA).

17. The prosthesis of claim 14, wherein the hydrophilic foam is selected from the group consisting essentially of poly(urethane), poly(ethylene), poly(vinyl alcohol), poly (acrylonitrile) hydrogel, styrene/poly(vinyl-pyrolodone) (PVP) copolymer, and poly(acrylic) acid copolymer.

18. The prosthesis of claim 10, wherein the anchoring structure and the support ring are stent structures.

* * * * *